United States Patent
Sarstedt

[11] Patent Number: 5,975,313
[45] Date of Patent: Nov. 2, 1999

[54] BLOOD-TUBE CAP WITH COAGULANT ADDITIVE

[75] Inventor: Walter Sarstedt, Nümbrecht, Germany

[73] Assignee: Sarstewdt AG & Co., Numbrecht, Germany

[21] Appl. No.: 09/017,080

[22] Filed: Feb. 2, 1998

[30] Foreign Application Priority Data

Feb. 3, 1997 [DE] Germany ............................ 197 03 921

[51] Int. Cl.⁶ .............................. B01D 65/00; B01L 3/00
[52] U.S. Cl. .......................... 210/456; 210/398; 215/247; 215/316; 422/102
[58] Field of Search .................................. 210/398, 456; 215/247, 294, 316, DIG. 3; 422/102

[56] References Cited

U.S. PATENT DOCUMENTS

| | | |
|---|---|---|
| 3,322,114 | 5/1967 | Portnoy . |
| 3,929,646 | 12/1975 | Adler .................................... 210/359 |
| 4,083,788 | 4/1978 | Ferrara ................................. 210/516 |
| 4,492,634 | 1/1985 | Villa-Real ............................. 210/398 |
| 4,652,429 | 3/1987 | Konrad .................................. 422/102 |
| 4,664,274 | 5/1987 | Konrad .................................. 215/232 |
| 5,308,506 | 5/1994 | McEwen et al. ....................... 210/745 |

FOREIGN PATENT DOCUMENTS

| | | |
|---|---|---|
| 0 086 456 | 8/1983 | European Pat. Off. . |
| 0 093 272 | 11/1983 | European Pat. Off. . |
| 30 18 262 | 11/1981 | Germany . |
| 195 19 886 | 12/1995 | Germany . |
| 44 02 690 | 9/1996 | Germany . |

*Primary Examiner*—John Kim
*Attorney, Agent, or Firm*—Herbert Dubno; Andrew Wilford

[57] ABSTRACT

A blood-tube cap has a generally tubular collar having a front end adapted to fit with a needle holder and a rear end adapted to fit with a blood tube and forming an axially extending passage between its ends, a pierceable membrane in the passage adjacent the front end, a flow-calming body in the passage rearward of the membrane, and a coating of a blood-reacting substance on the body. The passage is generally cylindrical and centered on an axis and the body is wedged in the passage. Furthermore the body is of cruciform cross section so as to leave spaces around itself through which the blood can flow, while effectively contacting the coating substance.

3 Claims, 1 Drawing Sheet

BLOOD-TUBE CAP WITH COAGULANT ADDITIVE

SPECIFICATION

1. Field of the Invention

The present invention relates to a cap used on a blood-sampling tube. More particularly this invention concerns such a cap used between a blood tube in which blood is collected and, often, centrifuged, and a needle holder that is inserted into a patient's blood vessel.

2. Background of the Invention

A standard blood-collecting kit comprises a sampling tube or vial having an open end, a cap fitted over this end and having a pierceable membrane, and a needle holder that is in turn fitted to the cap. The needle assembly comprises a luer collar fitted with a double-ended cannula or needle whose front end is inserted through the patient's skin normally into a vein from which blood is to be drawn. The cap has a luer fitting that fits complementary with the collar of the needle with the rear end of the needle poking through the membrane, and the opposite side of the cap is normally threaded to fit on the collection tube. When fully assembled with the front needle end inserted into a blood vessel, blood is drawn through the cannula into the tube. Once the tube is full, it can be unscrewed and another tube similarly filled, if desired.

It is known from my German patent 4,402,690 and from U.S. Pat. No. 4,492,634 of Villa-Real to substantially evacuate the sampling or collection tube so that once flow is established, blood runs into it without substantial foaming. Alternately a piston is provided that can be withdrawn into an extreme rear position in which it is latched so that, as it is moved back, it creates the desired underpressure that draws in the blood without substantial foaming. A baffle may be provided in the tube to intercept the blood flow therein and further reduce foaming.

The problem with this system is that it is often necessary to mix something with the blood right in the collection tube. Heparin is frequently used to prevent the blood from coagulating. With these systems the coagulant additive is provided at the base of the tube and does not mix well with the blood, requiring the user to shake it to achieve the desired mix. On the one hand such shaking can lead to problems such as leakage and is not generally considered safe. On the other hand if the blood is not mixed with the coagulant or other additive immediately, while still fresh, the desired reaction will not be achieved.

Accordingly as described in German patent document 195 19 886 of T. Shepard (U.S. equivalent patent application 254,720 of Jun. 6, 1994, U.S. Pat. No. 5,511,558) it is known to provided on the cap a compartment that can be traversed by the cannula and that contains the desired blood agent. The needle is poked through this compartment to open it up into the sample tube, then the needle is retracted so that the blood flows into the compartment to mix with the powder therein. Then the blood flows via the hole created earlier in a wall of the compartment by the needle into the tube. While such a system does ensure relatively good mixing of the fresh blood with the powder, it is a relatively complex construction that adds perceptibly to the manufacturing costs of the cap, which is a mass-produced item intended for a single use.

OBJECTS OF THE INVENTION

It is therefore an object of the present invention to provide an improved cap for a blood-sampling tube.

Another object is the provision of such an improved cap for a blood-sampling tube which overcomes the above-given disadvantages, that is which suppresses foaming while insuring good mixing of the incoming blood with a chemical agent such as an anticoagulant.

SUMMARY OF THE INVENTION

A blood-tube cap has according to the invention a generally tubular collar having a front end adapted to fit with a needle holder and a rear end adapted to fit with a blood tube and forming an axially extending passage between its ends, a pierceable membrane in the passage adjacent the front end, a flow-calming body in the passage rearward of the membrane, and a coating of a blood-reacting substance on the body.

Thus with this system the flow-calming body, which serves to prevent foaming of the blood as it pours into the tube, is coated with the desired substance, e.g. heparin, so that as the entering blood flows over and past it, this blood is thoroughly contacted with this substance. As a result the flow is calmed and the desired reacting agent is mixed with the blood.

According to the invention the passage is generally cylindrical and centered on an axis and the body is wedged in the passage. Furthermore the body is of cruciform cross section so as to leave spaces around itself through which the blood can flow, while effectively contacting the coating substance.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
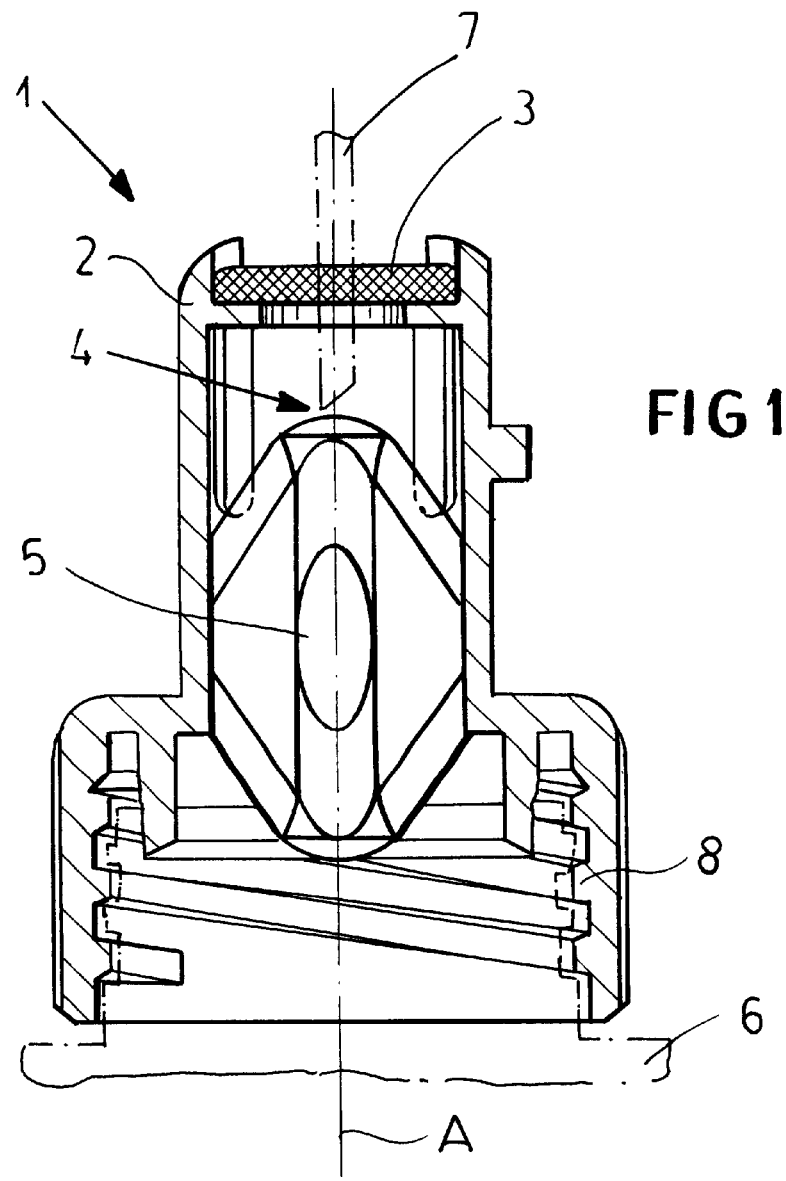
FIG. 1 is an axial section in enlarged scale through the cap according to the invention.
Figure 2:
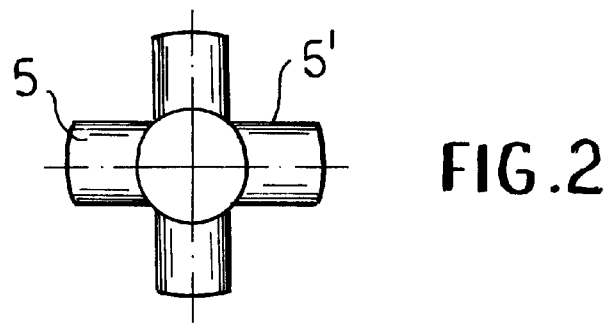
FIG. 2 is a top view of the coated deflecting body in accordance with the invention.

As seen in FIGS. 1 and 2 a cap 1 is intended to fit between a needle holder whose needle or cannula is shown in dot-dash lines at 7 and a blood-collecting tube shown partially in dot-dash lines at 6. The cap 1 is centered on an axis A and made of a molded plastic, with a rear end 8 formed with a screwthread that allows it to be solidly mounted on the tube 6 and a smaller cylindrical front-end extension 2 provided with a pierceable membrane 3. The cap 1 forms an axially throughgoing passage 4.

Internally according to the invention the cap 1 is provided with a plastic blood-calming body 5 made of plastic and of cruciform or X-shaped section that is provided with a coating 5' of a blood-reacting agent. This coating 5' can be a coagulant-inhibiting or -enhancing agent, here an anticoagulant such as heparin.

The solid cylindrical core of the body 5 is centered on the axis A in the extension 2 in which the body 5 is a snug pressure fit. Its four arms engage the inner surface of this extension 2 and define four subpassages via which blood can flow from the cannula 7 to the bottle 6.

I claim:

1. A blood-tube cap comprising:

a generally tubular collar having a front end adapted to fit with a needle holder and a rear end adapted to fit with a blood tube and forming an axially extending passage between its ends;

a pierceable membrane extending across and generally blocking the passage adjacent the front end;

a flow-calming body mounted in the collar in the passage rearward of the membrane; and a coating of a blood-reacting substance on the body.

2. The blood-tube cap defined in claim 1 wherein the passage is generally cylindrical and the body is wedged in the passage.

3. The blood-tube cap defined in claim 2 wherein the body is of cruciform cross section.

* * * * *